United States Patent
Lucas et al.

(10) Patent No.: US 7,794,673 B2
(45) Date of Patent: Sep. 14, 2010

(54) STERILIZER

(75) Inventors: James Lucas, Liverpool (GB); James Moruzzi, Wirral (GB)

(73) Assignee: Severn Trent Water Purification, Inc., Colmar, PA (US)

( * ) Notice: Subject to any disclaimer, the term of this patent is extended or adjusted under 35 U.S.C. 154(b) by 549 days.

(21) Appl. No.: 11/903,690

(22) Filed: Sep. 24, 2007
(Under 37 CFR 1.47)

(65) Prior Publication Data
US 2008/0131337 A1    Jun. 5, 2008

Related U.S. Application Data (63) Continuation-in-part of application No. 09/831,449, filed on Aug. 13, 2001, now abandoned.

(51) Int. Cl.
| | |
|---|---|
| *A61L 9/00* | (2006.01) |
| *A61L 2/00* | (2006.01) |
| *A62B 7/08* | (2006.01) |
| *B01J 19/08* | (2006.01) |
| *G01N 21/00* | (2006.01) |
| *G01N 23/00* | (2006.01) |

(52) U.S. Cl. .............. 422/186.3; 422/1; 422/5; 422/186; 422/292; 422/300; 422/307; 422/905; 422/906; 422/907; 250/454.11; 250/455.11

(58) Field of Classification Search ........ 422/1, 422/5, 21, 24, 121, 186, 186.3, 292, 300, 422/307, 905, 906, 907; 250/454.11, 455.11
See application file for complete search history.

(56) References Cited

U.S. PATENT DOCUMENTS 3,911,318 A * 10/1975 Spero et al. ............ 315/39
4,728,368 A    3/1988 Pedziwiatr
4,897,246 A    1/1990 Peterson
5,209,902 A * 5/1993 Matthews et al. ......... 422/21
6,028,315 A    2/2000 Bailey et al.

(Continued)

FOREIGN PATENT DOCUMENTS

GB    1 482 950    8/1977

(Continued)

OTHER PUBLICATIONS

USPTO Translation of JP 61-046290.*

(Continued)

*Primary Examiner*—Jill Warden
*Assistant Examiner*—Monzer R Chorbaji
(74) *Attorney, Agent, or Firm*—D'Ambrosio & Menon, LLP; Jo Katherine D'Ambrosio; Usha Menon (57) ABSTRACT

A lamp assembly comprising one or more lamp clusters. Each lamp cluster comprises one or more electrodeless UV lamps which are excited by microwaves emitted from a microwave generator. The microwave generator and power supply are enclosed within a housing that is integral with the lamp clusters. The lamp clusters are wholly surrounded by a waveguide. The waveguide, comprising a flange and a distal end cap connected by a mesh, forms an enclosure. The waveguide is essentially UV transparent to allow UV light to pass through but effectively opaque to microwaves in order to substantially contain the microwaves within the waveguide enclosure.

25 Claims, 4 Drawing Sheets

U.S. PATENT DOCUMENTS

| | | | |
|---|---|---|---|
| 6,080,270 A * | 6/2000 | Tabrez et al. | 156/345.36 |
| 6,348,669 B1 | 2/2002 | Rudd Little et al. | |
| 6,507,030 B1 | 1/2003 | Briggs et al. | |
| 6,693,382 B2 | 2/2004 | Little et al. | |
| 6,856,093 B2 | 2/2005 | Little et al. | |

FOREIGN PATENT DOCUMENTS

| | | | |
|---|---|---|---|
| JP | 61-046290 | * | 3/1986 |
| JP | 61-46290 | | 3/1986 |
| JP | 61-208743 | | 9/1986 |
| JP | 01-188424 | | 6/1991 |
| WO | WO 9609842 | | 4/1996 |
| WO | 9628840 | | 9/1996 |

OTHER PUBLICATIONS

Zakrytoe Akzionernoe Obschestv, Ultraviolet Vapour Lamp, Jul. 22, 2004, AU2003277761.

* cited by examiner

STERILIZER

CROSS REFERENCES TO RELATED CASES

This is a continuation in part of U.S. patent application Ser. No. 09/831,449, filed Aug. 13, 2001, abandoned contemporaneously with the filing of this application.

FIELD OF INVENTION

The present invention relates to disinfection systems using ultraviolet radiation, particularly disinfection systems having a UV lamp assembly.

BACKGROUND OF THE INVENTION

Ultraviolet (UV) radiation systems are used in the purification of water and the sanitization of a variety of items. The UV radiation and any ozone produced by the UV radiation act to kill bacteria and germs.

Traditional water disinfection systems using mercury UV lamps generate radiation through gas discharge. A critical component in the operation of mercury UV lamps is the pressure of the mercury. A UV lamp is filled with a gas containing low pressure mercury vapour and argon or xenon. When the microwaves are turned on, electrons are emitted. These electrons collide with and ionize noble gas atoms in the bulb to form a plasma by a process of impact ionization. As a result of avalanche ionization, the conductivity of the ionized gas rapidly rises, allowing higher currents to flow through the lamp. The mercury, which exists at a stable vapour pressure equilibrium point of about one part per thousand in the inside of the tube (with the noble gas pressure typically being about 0.3% of standard atmospheric pressure), is then likewise ionized, causing it to emit light in the ultraviolet (UV) region of the spectrum predominantly at wavelengths of 253.7 nm and 185 nm. The efficiency of the lamp owes much to the fact that low pressure mercury discharges emit about 65% of their total light at the 254 nm line. About 10-20% of the light emitted in UV is at the 185 nm line.

Another problem with traditional UV lamps is the high failure rate of the lamps and ballasts. The maintenance costs resulting from frequent lamp replacements is substantial. The UV output degrades over time. Additional stand-by systems are required to keep the systems running efficiently. Another problem with the existing UV systems is the lack of a mechanism to turn the systems on and off quickly. Typically traditional lamps can only be turned on and off four times a day. Frequent switching of traditional electroded lamps wears them out very quickly.

SUMMARY OF THE INVENTION

This invention comprises a UV lamp assembly and system which enables efficient, high UV treatment for fluid purification, i.e., sanitizing air, water and waste water, as well as sterilization of possibly contaminated solid items. The lamp assembly comprises one or more lamp clusters. Each lamp cluster is made up of one or more electrodeless UV lamps which are excited by a microwave generator. The microwave generator, for example, a magnetron, and switching power supply are either provided as separate components or are enclosed within a common housing that is an integral part of the lamp assembly. Alternatively, the microwave generator and power supply can be enclosed in separate housings. The lamp clusters are wholly surrounded by a waveguide. The waveguide, comprising a flange and a distal end cap connected by a mesh, forms an enclosure.

The waveguide of this invention is essentially UV transparent to allow UV light to pass through but effectively opaque to microwaves in order to substantially contain the microwaves within the waveguide. Containing the microwaves within the enclosure formed by the waveguide improves the disinfection qualities of the UV lamp assembly by emitting more UV rays to the surrounding fluids or solids. Because the waveguide is comprised of a conducting material, for example stainless steel, copper or brass, that blocks the path of the microwaves, the waveguide is able to substantially prevent microwaves from escaping thereby directing the bulk of the microwaves to the UV lamps for optimal UV output.

In another embodiment, the lamp assembly for use in a fluid purification or sterilization system further comprises a protective sleeve enclosing the waveguide. The sleeve is coaxial with the waveguide and is essentially transparent to UV rays to allow the UV rays to escape to the surrounding fluids. The sleeve can comprise a material impervious to fluids to protect the waveguide from the fluids, but at the same time allowing the emission of UV rays into the fluids. In one embodiment, the sleeve comprises quartz.

The quartz sleeve, however, prevents the ingress of fluids into the waveguide. In other embodiments, the lamp assemblies are grouped in multiples to form one or more lamp modules. Each lamp module can be switched on and off or, turned up or down, to match flow. The modular design is used to meet varying flow rates and disinfection demands. In yet a further embodiment, the lamp assembly comprises one or more lamp clusters. Preferably, the lamp clusters comprise one or more electrodeless ultraviolet ("UV") lamps. The electrodeless UV lamps are excited by microwaves to emit UV rays. The UV lamps emit monochromatic or polychromatic UV radiation. The dominant wavelength of the UV radiation is from 240 nm to 310 nm.

Advantageously, the waveguide comprises a shape and size to wholly surround the lamp clusters so as to substantially contain the microwaves within the waveguide. The waveguide further comprises a flange. In another embodiment, the waveguide further comprises a mesh comprising intersecting metallic filaments and an end cap. The mesh extends from the flange to the end cap. The intersecting metallic filaments of the mesh define holes. The holes comprise a size smaller than the wavelength of the microwaves so as to avoid microwave leakage. The flange, end cap and mesh of the waveguide, form an enclosure. The waveguide enclosure contains the microwaves transmitted by the microwave generator while allowing the emission of UV rays from the waveguide. The waveguide can have a cylindrical or rectangular form.

Preferably, the end cap is distal to the flange. The end cap further comprises perforations wherein the perforations comprise a size smaller than the size of the microwave wavelengths to substantially reduce microwave leakage from the lamp assembly. The end cap also has mounting means for attaching the electrodeless UV lamps to the waveguide.

A housing encloses a microwave generator. The housing is coupled to the waveguide by a flange. The microwave generator generates and transmits microwaves that excite the UV lamps. In one embodiment, the microwave generator comprises a magnetron. The housing further comprises a power supply for the microwave generator. The housing is releasably connected to the flange of the waveguide so as to allow for easy and quick detachment of the housing from the waveguide. This facilitates removal of the microwave generator or power supply contained within the housing making the system more cost effective to maintain and repair.

In another embodiment of the invention, a lamp assembly for use in a fluid sterilization system comprises one or more lamp clusters. Advantageously, the lamp clusters have one or more electrodeless UV lamps for receiving microwaves. A cylindrical waveguide wholly surrounds the lamps clusters to substantially contain the microwaves within the waveguide. The waveguide preferably is made of a conducting material, for example stainless steel, copper or brass. The waveguide comprises at least a flange, an end cap and a mesh that connects the flange and the end cap.

The lamp assembly further comprises a launcher in connection with the microwave generator and releaseably attached to the flange. The launcher receives microwaves from the microwave generator and transmits the microwaves to the waveguide enclosure to stimulate the UV lamps. The waveguide contains the microwaves while allowing emission of UV light to the outside fluids. The waveguide is devoid of a resonant cavity.

Another embodiment of this invention comprises a fluid sterilization system comprising an outer housing having an inlet and an outlet. The outer housing is shaped to guide fluid flow from the inlet, past the waveguide to the outlet. One or more lamp clusters are positioned within the outer housing. The lamp clusters comprise one or more electrodeless UV lamps. The UV lamps are excited by microwaves to emit UV rays. The invention further comprises a housing comprising a microwave generator and a power source to light the lamps. Alternatively, the generator and power source can be in separate housings. Microwaves from the microwave generator are transmitted to the electrodeless UV lamps through a waveguide. The waveguide is dimensioned to wholly surround the lamp clusters. The waveguide comprises a flange. The inner housing is releasably connected to the waveguide flange. The waveguide is enclosed by a sleeve. The sleeve is essentially transparent to UV rays and is coaxial with the waveguide.

In another embodiment, the invention comprises a modular lamp assembly. One or more lamp assemblies are grouped in selective multiples to form one or more modules. Each lamp assembly comprises one or more lamp clusters. The lamp clusters comprise one or more electrodeless UV lamps. Preferably, the electrodeless UV lamps have an elongate form. The electrodeless lamps are excited by microwaves to emit UV rays. Advantageously, the microwaves are contained within a waveguide that has a size and shape to wholly surround the lamp clusters. The waveguide further comprises a flange. A housing comprising a microwave generator is releasably coupled to the waveguide flange. The microwave generator generates and transmits microwaves that excite the UV lamps.

Each module comprises an on/off switch such that each module can be powered individually to facilitate energy savings and control flow pacing. The modular lamp assembly further comprises one or more UV sensors to measure UV power or intensity in the surrounding fluid. Blower fans can be used to cool the lamps as air passes over them. The optimum temperature for the environs surrounding the lamp clusters is between 45° C. to 70° C.

DETAILED DESCRIPTION OF THE PREFERRED EMBODIMENTS

The lamp assembly and system of the present invention is used to treat water, waste water and air for both human consumption and industrial process. It also sterilizes solid items that may be contaminated. The process of purification or fluids or sterilization of items is achieved by exposure to UV radiation. A high frequency current in the form of microwaves is applied to electrodeless UV lamps. The lamp assembly is wholly surrounded by a waveguide that traps the microwaves within the waveguide enclosure. In this way, the microwaves travel the full length of the UV bulbs to stimulate the entire bulb to emit UV rays.

The microwaves collide with and ionize the gas atoms within the UV lamps to form a plasma by a process of impact ionization. As a result of avalanche ionization, the conductivity of the ionized gas rapidly rises, allowing higher currents to flow through the lamp. The mercury within the UV lamp is likewise ionized to emit light in the UV region of the spectrum, predominantly at the germicidal wavelength of 253.7 nm.

Figure 1:
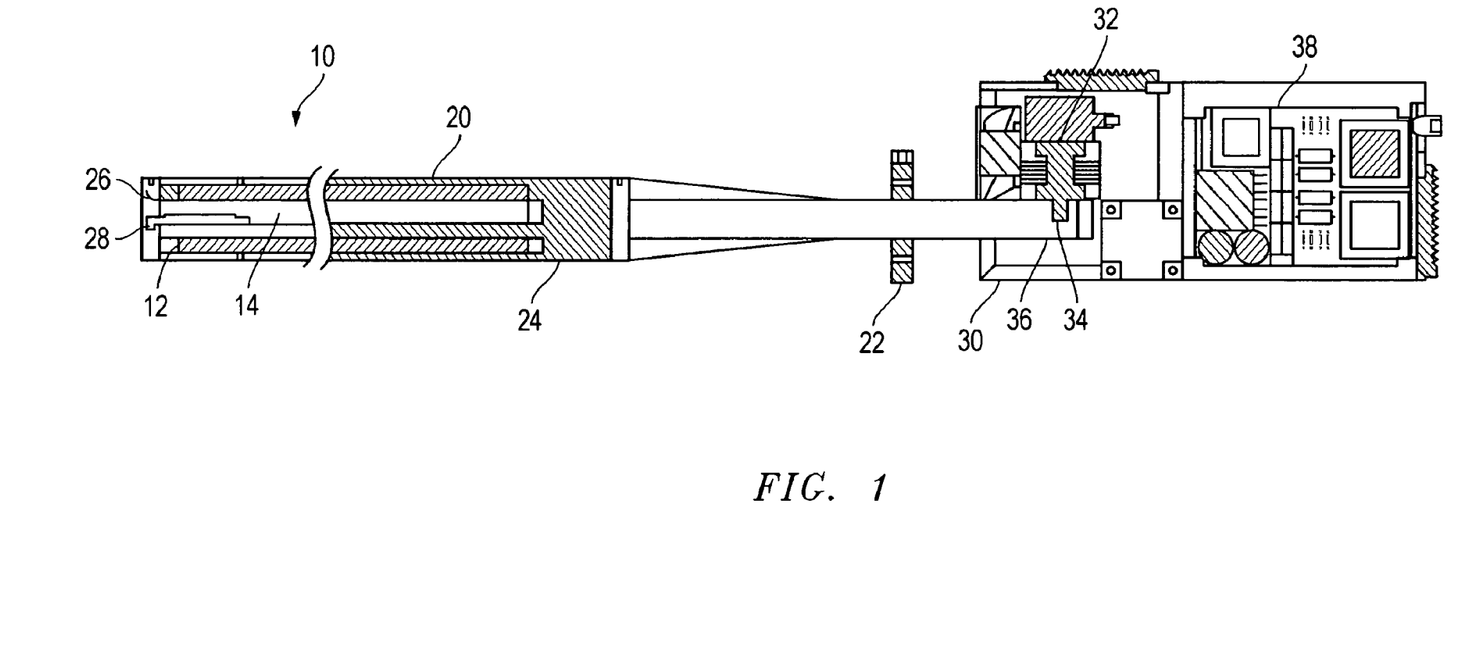
FIG. 1 is a cross section of the lamp assembly of the invention.

In one embodiment of the apparatus of this invention, shown in FIG. 1, a lamp assembly 10 comprises one or more lamp clusters 12. Each lamp cluster 12 has one or more electrodeless UV lamps 14. The use of electrodeless UV lamps 14 results in better reliability because there are no electrodes that may fail. The electrodeless UV lamps 14 are not subject to the same fade seen in traditional UV lamps. The electrodeless UV lamps 14 typically last for around 3 years. Their longer life span means fewer lamps will be disposed on a yearly basis as compared to other UV lamp systems. In addition, the electrodeless UV lamps 14 contain a small amount of mercury, which, in large quantities is a environmental contaminant. Typically, electrodeless UV lamps 14 contain 5 to 15 mg of mercury. Therefore, the electrodeless UV lamps 14 are more environmentally friendly. Other advantages of microwave powered electrodeless UV lamps are known in the art.

The electrodeless UV lamp 14 comprises a partially evacuated tube. The tube further comprises an element or mixtures of elements in vapor form. Mercury is a preferred element for this purpose, but alternatives include mixtures of inert gases with mercury compounds, sodium and sulphur. Halides, such as mercury halide are also suitable herein. Amalgams are also suitable herein including indium/mercury amalgam. The elements or mixtures of elements when excited by microwaves emit monochromatic or polychromatic UV radiation. The electrodeless UV lamp 14 has any suitable shape and size, including elongate forms such as a cigar-shape. In other embodiments, the lamps have other shapes such as flat, double skinned or globe shaped. The electrodeless UV lamp 14 size can be customized for the application. Typical lamp diameters range from 5 to 200 mm, preferably within a range of 19-38 mm.

Preferably, the peak operating energy of the electrodeless UV lamp 14 is from 100 watts to 100,000 watts, preferably from 500 watts to 30,000 watts. The dominant wavelength of electrodeless UV lamps 14 may be selected according to the particular application for which the lamp assembly 10 is to be used. In one embodiment, the dominant wavelength of the electrodeless UV lamps 14 is from 240 nm to 310 nm. Such wavelengths have been found to be particularly useful for sterilization, purification or sanitization applications.

In another aspect, the dominant wavelength of the electrodeless UV lamps 14 is from 140 to 260 nm. Such wavelengths have been found to be particularly useful for use in promoting molecular dissociation reactions. Alternatively, the dominant wavelength of the electrodeless UV lamps 14 ranges from 310 to 400 nm, preferably from 320 to 380 nm. Such wavelengths have been found to be particularly useful for use in promoting certain photochemical reactions.

One problem with previous UV radiation systems using UV lamps is the leakage of microwaves from the lamp clusters 12. Advantageously, the lamp clusters 12 of the present invention are wholly surrounded by a waveguide 20 to substantially contain and trap the microwaves within the enclosure formed by the waveguide 20. Although the waveguide is essentially UV transparent to allow the UV rays to be emitted to the surrounding environment, the waveguide 20 is preferably comprised of a conducting material, for example stainless steel, copper or brass that is relatively opaque to microwaves. Consequently, the substantially microwave-opaque waveguide 20 essentially blocks the path of the microwaves thereby preventing the bulk of the microwaves from escaping.

Because the waveguide 20 blocks the escape of the microwaves, the majority of the microwaves are directed to the UV lamps 14 for optimal UV output. The waveguide 20 is comprised of a flange 22, an end cap 26 distal to the flange 22 and a mesh 24 extending from the flange 22 to the end cap 26. The waveguide 20 forms a substantially microwave-opaque enclosure surrounding the lamp clusters 12. The waveguide 20 is dimensioned, that is, comprises a size and shape to wholly surround the one or more lamp clusters 12 so as to substantially contain the microwaves within the waveguide 20. The end cap 26 further, comprises mounting means 28 for the electrodeless UV lamps 14. The waveguide 20 enclosure contains the microwaves transmitted by the microwave generator 32 while allowing the emission of UV rays from the waveguide 20. The waveguide 20 can have a cylindrical or rectangular form. A waveguide 20 restricts the three dimensional "free space" propagation of the electromagnetic wave to a single dimension. waveguides are:

Low loss: meaning that the wave travels along the guide without greatly attenuating as it goes.

Routable. this means that the guiding structure can be bend gently without losing contact with the wave, without generating reflections, and without incurring additional loss.

The waveguide 20 is optically transparent, that is, it is substantially transparent to the ultraviolet radiation employed herein, typically having a transparency of greater than 50%, preferably greater than 90% to UV radiation. The waveguide 20 controls the flow of ultraviolet radiation therefrom. The control function includes the prevention of the release of harmful or unnecessary ultraviolet radiation frequencies. As described above, the waveguide 20 blocks at least the majority of the flow of microwave energy therefrom and directs the microwave energy to the lamp clusters 12.

Figure 2:
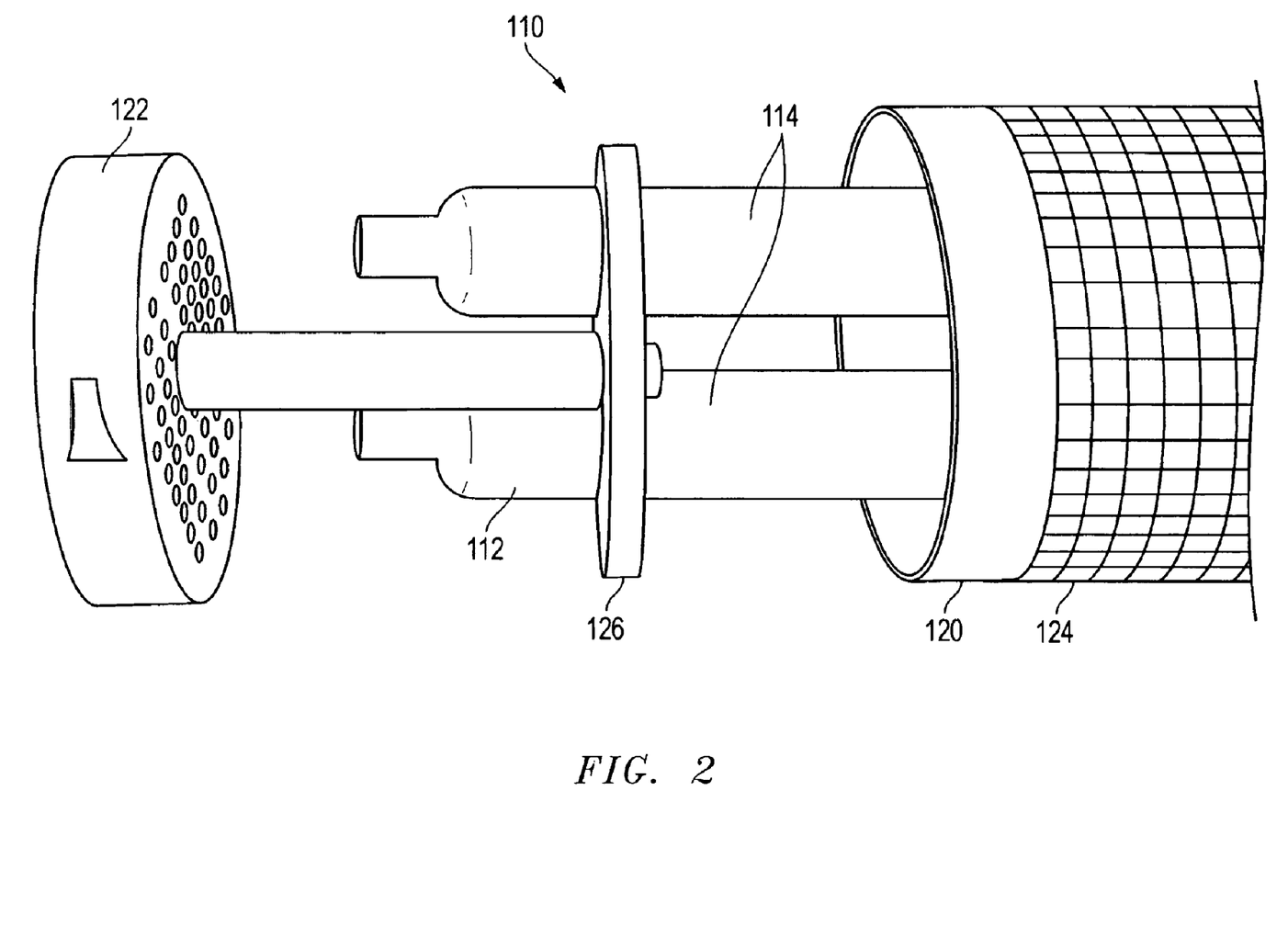
FIG. 2 is a side view of the lamp assembly of the invention.

FIG. 2 shows another view of the lamp assembly 110. The waveguide 120 comprises a mesh 124 of intersecting metallic filaments. The intersecting metallic filaments define holes. The diameters of the holes are sized smaller than the microwave wavelengths to avoid microwave leakage. The waveguide mesh 124 is constructed to ensure control of the escape of microwaves. For example, the waveguide 120 can be adapted to include different hole spacings, wire thicknesses and overall configurations.

Referring now to both FIG. 1 and FIG. 2, the waveguide 20, 120 comprises conductive material comprising brass, copper or stainless steel or other conductive material. The conducting material may be integral, or applied as an internal or external coating (or liner) to the quartz sleeve. The liner may directly contact the inner surface of the quartz sleeve or be spaced therefrom.

By blocking the escape of the microwaves, the waveguide 20, 120 contains and directs the microwaves to the lamp clusters 12, 112, thereby maximizing the efficiency of the UV lamp assembly 10, 110. Different configurations of waveguide 20 can be envisioned. In one embodiment, the waveguide 20 120 is cylindrical in form. Rectangular waveguides can be used, especially for disinfecting solids. The waveguide 120 further comprises an end cap 122. The end cap 122 is perforated. The perforations comprise a size smaller than the size of the microwave wavelengths to substantially reduce the microwave leakage from the lamp assembly 110. The end cap 122 further comprises mounting means 126 to attach the lamp clusters 112 to the waveguide 20.

Referring back to FIG. 1, a housing 30 is releasably coupled to the waveguide flange 22. The housing 30 can enclose a microwave generator 32, a launcher 36 and a power source 38. Alternatively, the power source 38 can be contained within a separate housing (not shown.) The microwave generator 32 preferably comprises a magnetron. The magnetron has an antenna 34 which transmits the generated microwaves to the waveguide 20 using the launcher 36 as a pathguide. In one embodiment, the antenna 34 extends into the launcher and the launcher 36 receives microwaves from the microwave generator 32. The launcher 36 is releasebly connected to the waveguide flange 22. Microwaves generated within the housing 30 leave the generator by means of the antenna 34, enter the launcher 36 and then are transmitted to the waveguide 20. In one embodiment, the launcher is a solid, conducting material.

The lamp assembly can further comprise a power source 38 for powering the microwave generator 32. Preferably, the power source 38 comprises a 240v single phase. A power source 38 is able to power the lamp clusters 12, facilitate flow pacing since it has an unlimited ability to be turned on and off and powered up and down, and monitor the electrodeless UV lamps 14. Since the lamps are electrodeless, there are no electrical connections required between the microwave generator and the lamps. Advantageously, since the power source 38 is contained within a housing, no power comes in contact with any outside fluids.

The microwave generator housing 30 is releasably coupled with the waveguide 20 such that, if the power source 38 is within the same housing, and required replacement, the housing can be easily detached and the power source replaced from within the housing 30. The housing 30 can then be re-coupled with the waveguide 20.

The microwave generator 32 provides microwave energy to excite the electrodeless UV lamps 14. In one embodiment, the microwaves are continuous (i.e. non-pulsed) microwaves. In an alternative embodiment, the microwave generator 32 can be pulsed with pulse widths ranging from 100 milliseconds to 0.5 microseconds, preferably from 10 milliseconds to 5 microseconds. The microwave energy source has a pulse period of from 100 milliseconds to 0.5 microseconds, preferably from 5 milliseconds to 50 microseconds. Microwave energy can be pulsed at a frequency of from 2 MegaHertz to 10 Hertz by the microwave generator 32. In still another embodiment, the electrodeless UV lamps 14 are excited by both a continuous microwave generator and a pulsed microwave generator.

Figure 3:
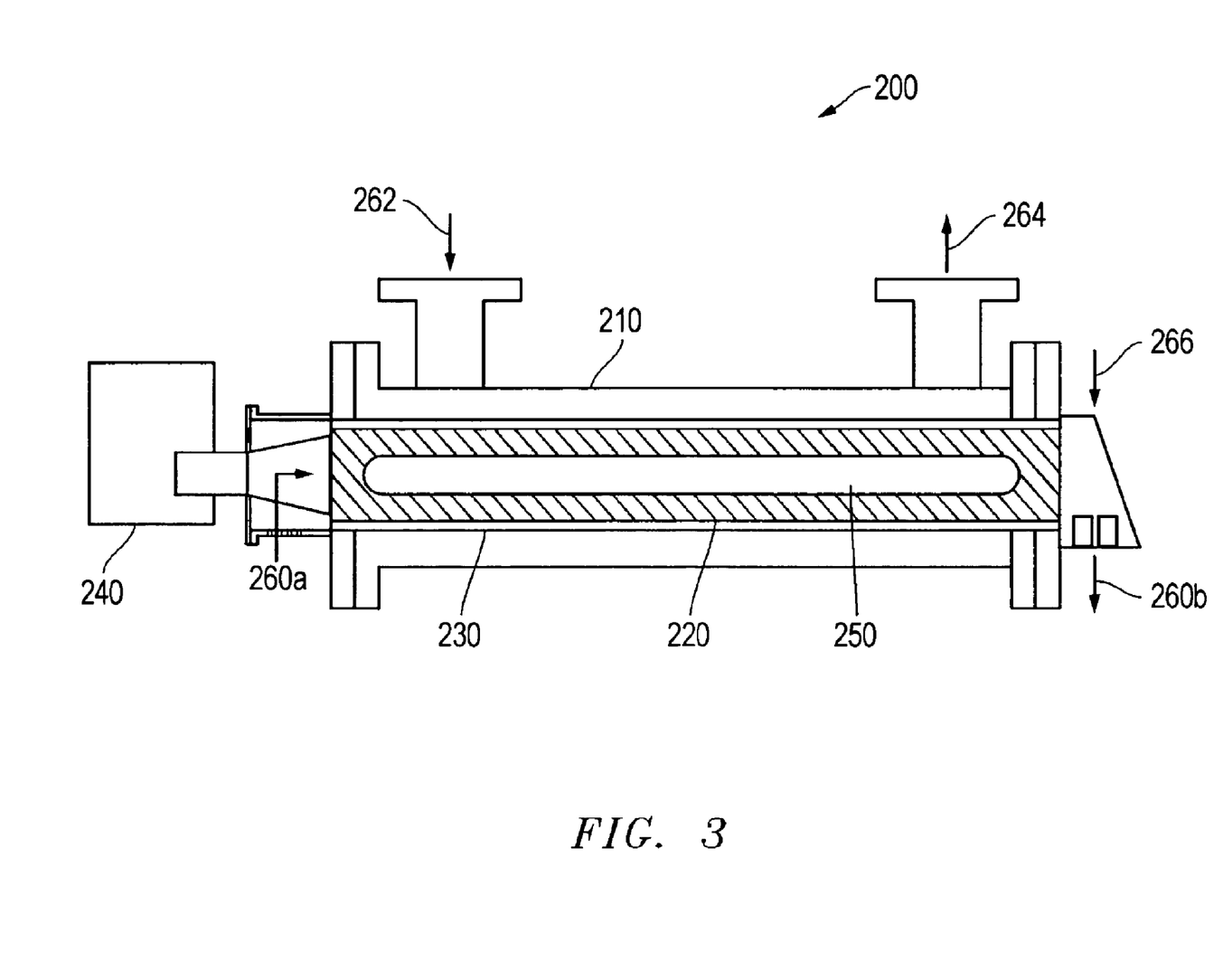
FIG. 3 is a side view of the lamp assembly for use in a fluid sterilization system.

FIG. 3 shows another embodiment of the lamp assembly enclosed within a vessel; this embodiment is useful for fluid sterilization. Preferably, the fluid comprises air or a liquid such as water or wastewater. A fluid sterilization system 200 comprises tubular closed vessel 210 for enclosing the lamp clusters. The closed vessel 210 has a fluid inlet 262 and a fluid outlet 264 provided thereto. Suitably, the fluid sterilization system 200 additionally comprises a pump for pumping fluid from the inlet 262, past the waveguide 220 to the outlet 264. Alternatively, gravity may be utilized to encourage fluid flow.

One or more electrodeless lamps 250 are wholly surrounded by an UV transparent waveguide 220. The waveguide 220 is surrounded by a sleeve 230 essentially transparent to UV rays. The sleeve 230 comprises a material, preferably quartz, that prevents the ingress of fluids into the waveguide 220. The sleeve 230 is coaxial with the waveguide 220. The sleeve 230 allows emission of UV rays into the fluids. A flow of air 260a, 260b is maintained through the sleeve 230 to prevent the build up of heat within the lamp assembly. The lamp assembly further comprises a housing 240 for enclosing a microwave generator and, in one embodiment, the power source. Alternatively, the power source is contained within a separate housing. The fluid sterilization system 200 further comprises a cooling fan box 266 for cooling the electrodeless UV lamp 250.

The outer circumference of the lamp clusters maintain the same ambient temperature of the fluids. The electrodeless UV lamp 250 inside the sleeve 230 will run at an operating temperature of 60-80° C. This has an additional benefit of reducing fouling of the sleeve compared to UV systems running at high temperatures.

The choice of materials for use in the closed vessel 210 and any fluid flow piping arrangements can be important. Typically, the materials will be selected which are resistant to corrosion and which do not leach contaminants to the system. Seal materials are also carefully selected with typical seal materials including Chemraz (trade name), Teflon (trade name), encapsulated Viton (trade name) and GORE-TEX (trade name).

Figure 4:
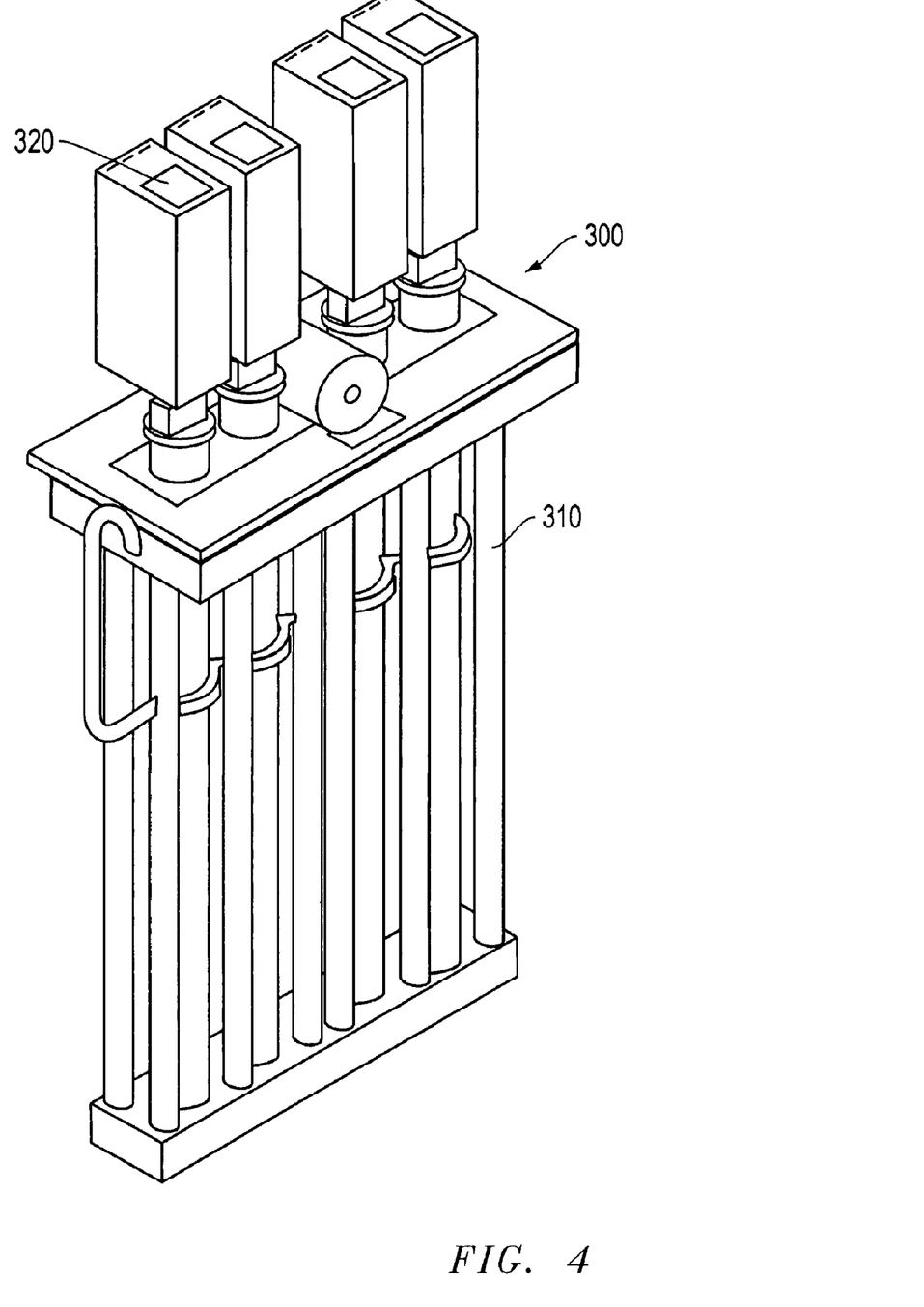
FIG. 4 is a depiction of a modular lamp assembly of the invention.

In use, fluid flows from the inlet 262 past the waveguide 220 and towards the outlet 264. As the fluid flows past the waveguide 220 it is irradiated with UV radiation produced by the electrodeless UV lamp 250. The radiation itself passes through the UV transparent walls of the waveguide 220 and sleeve 230 to contact the fluid. FIG. 4 shows a modular lamp assembly of this invention. One or more lamp assemblies 310 are grouped in selective multiples to form a modular lamp assembly 300. The lamp assemblies 300 comprise on/off switches 320 that can be individually powered to control flow pacing and control disinfection properties. In another embodiment, UV sensors measure the UV output. Preferably, the modular lamp assembly 310 comprises at least one UV sensor.

The lamp assembly of the invention is suitable for use in sterilizing a variety of substances including water for human consumption as well as industrial processes and waste water and sewage when used within water or other liquid outer housings. Several of the embodiments as described and illustrated in the figures, can also be used to sanitize air, for example air in buildings such as hospitals, offices and homes. These embodiments can also be easily adapted to sterilize solid objects both metallic and non-metallic objects such as medical instruments; as well as used to prolong the shelf-life of foodstuffs (e.g. fruit and vegetables) by killing bacteria on the surface thereof.

The foregoing description is illustrative and explanatory of preferred embodiments of the invention, and variations in the method, systems and other details will become apparent to those skilled in the art. It is intended that all such variations and modifications which fall within the scope or spirit of the appended claims be embraced thereby.

The invention claimed is:

1. A lamp assembly comprising:
    one or more lamp clusters, each lamp cluster comprising one or more electrodeless ultraviolet lamps for receiving microwaves;
    a waveguide comprising a shape and size to wholly surround the lamp clusters so as to substantially contain the microwaves within the waveguide, the waveguide further comprising a flange and an end cap distal to the flange, the end cap further comprising perforations, the perforations having a size smaller than the size of microwave wavelengths to substantially reduce microwave leakage from the lamp assembly; and
    a housing coupled to the flange, the housing comprising a microwave generator for generating and transmitting microwaves to excite the UV lamps to emit UV rays.

2. The lamp assembly of claim 1, wherein the end cap comprises mounting means for mounting the electrodeless ultraviolet lamps.

3. The lamp assembly of claim 1, wherein the UV lamps emit monochromatic or polychromatic ultraviolet radiation.

4. The lamp assembly of claim 1, wherein the dominant wavelength of the ultraviolet radiation is from 240 nm to 310 nm.

5. The lamp assembly of claim 1, wherein the waveguide is essentially transparent to UV radiation and substantially opaque to microwaves.

6. The lamp assembly of claim 1, wherein the waveguide further comprises a mesh, the mesh comprises intersecting filaments, the intersecting metallic filaments defining holes, the holes comprising a size smaller than the wavelength of the microwaves to avoid microwave leakage.

7. The lamp assembly of claim 6, wherein the mesh extends from the end cap to the flange.

8. The lamp assembly of claim 1, wherein the waveguide comprises a conducting material, the conducting material being essentially UV transparent and substantially microwave opaque so that the waveguide contains the microwaves received from the microwave generator and directs the microwaves to excite the lamp clusters positioned within the waveguide enclosure while allowing the UV rays emanating from the lamp cluster to be emitted from the waveguide.

9. The lamp assembly of claim 1, wherein the waveguide has a cylindrical or rectangular form.

10. The lamp assembly of claim 1, wherein the microwave generator comprises a magnetron.

11. The lamp assembly of claim 1, wherein the housing further comprises a power source for the microwave generator.

12. The lamp assembly of claim 1, further comprising a sleeve, the sleeve essentially transparent to ultraviolet light, the sleeve surrounding the lamp clusters and coaxial with the waveguide.

13. A lamp assembly for use in a fluid sterilization system, the lamp assembly comprising:
    one or more lamp clusters, the lamp clusters comprising one or more electrodeless ultraviolet lamps for receiving microwaves;

a substantially microwave-opaque waveguide wholly surrounding the lamp clusters to form a waveguide enclosure, the waveguide blocking the escape of the microwaves so as to substantially contain the microwaves within the waveguide enclosure thereby directing the microwaves to the lamp clusters;

the waveguide comprising a flange, an end cap and a mesh, the mesh extending from the flange to the end cap, the end cap distal to the flange, the end cap further comprising perforations, the perforations having a size smaller than the size of microwave wavelengths to substantially reduce microwave leakage from the lamp assembly, the waveguide allowing emission of UV rays to the fluids;

a housing releasably coupled to the flange, the housing comprising a microwave generator, for generating and transmitting microwaves to excite the UV lamps to emit UV rays;

a power source to light the UV lamps; and a sleeve essentially transparent to UV rays, the sleeve enclosing the waveguide and coxial with the waveguide, the sleeve comprising a material impervious to fluids to protect the waveguide from the fluids while allowing the emission of UV rays into the fluids.

14. The lamp assembly of claim 13, wherein one or more lamp assemblies are grouped in selective multiples to form one or more modules.

15. The lamp assembly of claim 13, wherein the housing further comprises a launcher for transmitting microwaves from the microwave energy generator to the waveguide.

16. The lamp assembly of claim 13, wherein the sleeve comprises quartz.

17. The lamp assembly of claim 13, wherein the housing further enclosing the power source.

18. The lamp assembly of claim 13, wherein the waveguide is devoid of a resonant cavity.

19. A fluid sterilization system comprising:

a closed vessel system having an inlet and an outlet;

one or more lamp clusters positioned within the closed vessel system, each lamp cluster comprising one or more electrodeless ultraviolet lamps for receiving microwaves;

a waveguide comprising a size and shape to wholly surround the lamp clusters to substantially enclose the microwaves within the waveguide, the waveguide further comprising a flange and an end cap distal to the flange, the end cap further comprising perforations, the perforations having a size smaller than the size of microwave wavelengths to substantially reduce microwave leakage from the fluid sterilization system;

a sleeve essentially transparent to UV rays, the sleeve enclosing the waveguide and coxial with the waveguide, the sleeve comprising a material impervious to fluids to protect the waveguide from the fluids while allowing the emission of UV rays into the fluids; and a housing, the housing comprising a microwave generator for generating and transmitting microwaves to excite the UV lamps to emit UV rays and an antenna extending from the microwave generator to transmit the microwaves;

a power source to light the UV lamps; and a launcher releaseably connected to the flange, the launcher positioned adjacent to antenna to receive the microwaves and transmit the microwaves from the antenna to the waveguide.

20. The fluid sterilization system of claim 19, wherein the closed vessel is shaped to guide fluid flow from the inlet, past the waveguide to the outlet.

21. The fluid sterilization system of claim 19, wherein the end cap further comprising mounting means for mounting the electrodeless ultraviolet lamps.

22. A modular lamp assembly comprising:

one or more lamp assemblies grouped in selective multiples to form one or more modules;

the one or more lamp assemblies comprising at least one or more electrodeless UV lamps for receiving microwaves from a microwave generator;

an essentially UV transparent, substantially microwave-opaque waveguide wholly surrounding the electrodeless UV lamps to substantially contain the microwaves within the waveguide and direct the UV rays to the UV lamps;

the waveguide comprising an end cap, a flange and a mesh connecting the flange to the end cap to enclose the one or more UV lamps, the end cap distal to the flange, the end cap further comprising perforations, the perforations having a size smaller than the size of microwave wavelengths to substantially reduce microwave leakage from the modular lamp assembly;

a sleeve essentially transparent to UV rays enclosing the waveguide and coaxial with the waveguide, and a housing comprising a microwave generator releasably coupled to the waveguide flange.

23. The modular lamp assembly of claim 22, wherein each module comprises an power switch so that each module can be powered individually.

24. The modular lamp assembly of claim 22, wherein the waveguide comprises a conducting material.

25. The modular lamp assembly of claim 22, wherein the sleeve comprises quartz.

* * * * *